United States Patent [19]

Vaillancourt

[11] Patent Number: 4,863,431
[45] Date of Patent: Sep. 5, 1989

[54] CATHETER ASSEMBLY

[76] Inventor: Vincent L. Vaillancourt, 14 Bunyan Dr., Livingston, N.J. 07039

[21] Appl. No.: 163,647

[22] Filed: Mar. 3, 1988

[51] Int. Cl.⁴ .............................................. A61M 5/00
[52] U.S. Cl. ................................... 604/168; 604/170; 128/658
[58] Field of Search ............... 604/164, 165, 167, 168, 604/170, 171; 128/772, 658

[56] References Cited

U.S. PATENT DOCUMENTS

| | | | |
|---|---|---|---|
| 4,193,399 | 3/1980 | Robinson | 604/168 |
| 4,417,886 | 11/1983 | Frankhouser et al. | 604/164 X |
| 4,509,945 | 4/1985 | Kramann et al. | 604/164 |
| 4,525,157 | 6/1985 | Vaillancourt | 604/165 X |
| 4,655,750 | 4/1987 | Vaillancourt | 604/168 X |

Primary Examiner—Stephen C. Pellegrino
Attorney, Agent, or Firm—Kenyon & Kenyon

[57] ABSTRACT

The catheter assembly employs a catheter unit, a needle unit and a guide wire unit which has a guide wire located within the hollow needle of the needle unit in the retracted position of the needle unit. The guide wire is initially spaced about three to six millimeters from the distal end of the hollow needle and can be inserted into a vessel over a distance of about one-half inch. The needle unit has a flashback chamber which is sealed by the guide wire unit to prevent outflow of blood.

22 Claims, 3 Drawing Sheets

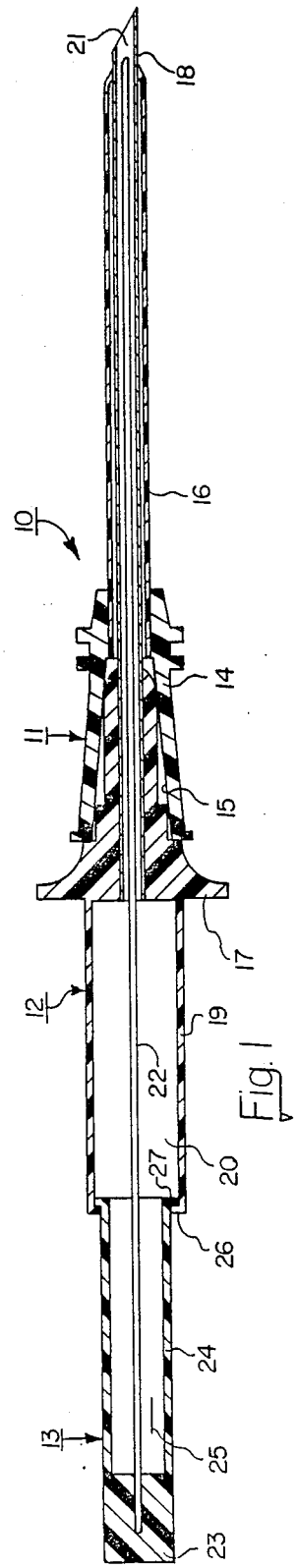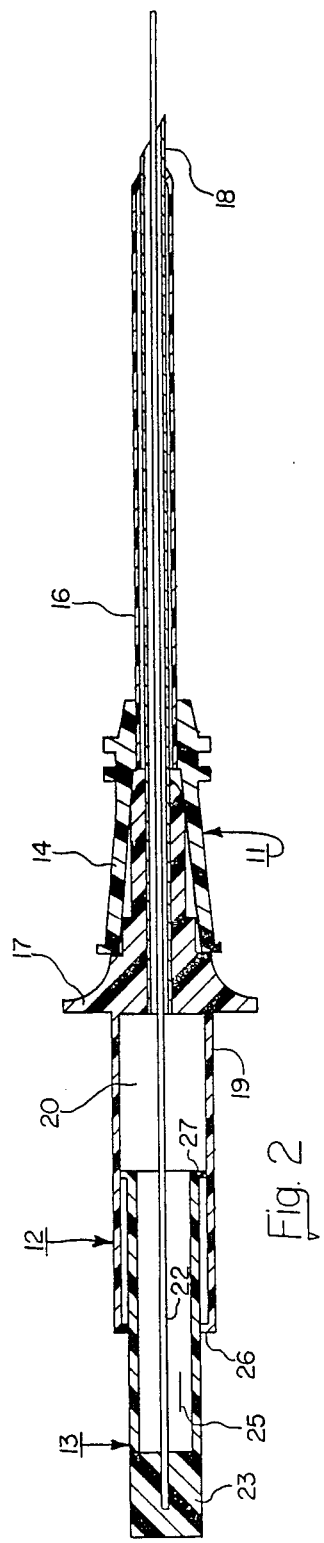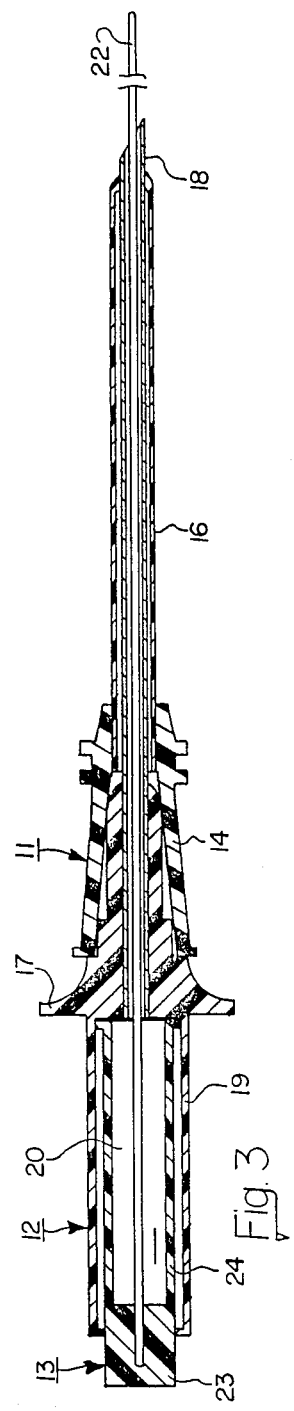

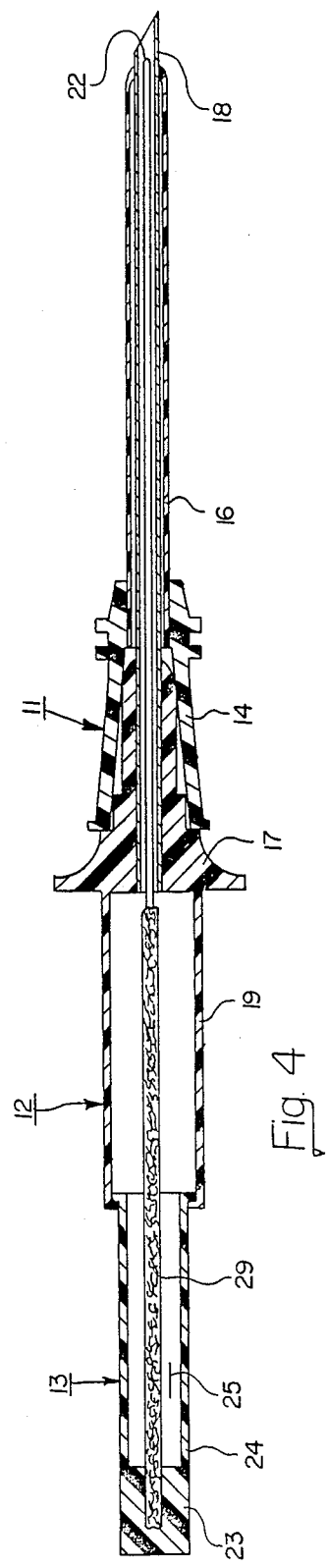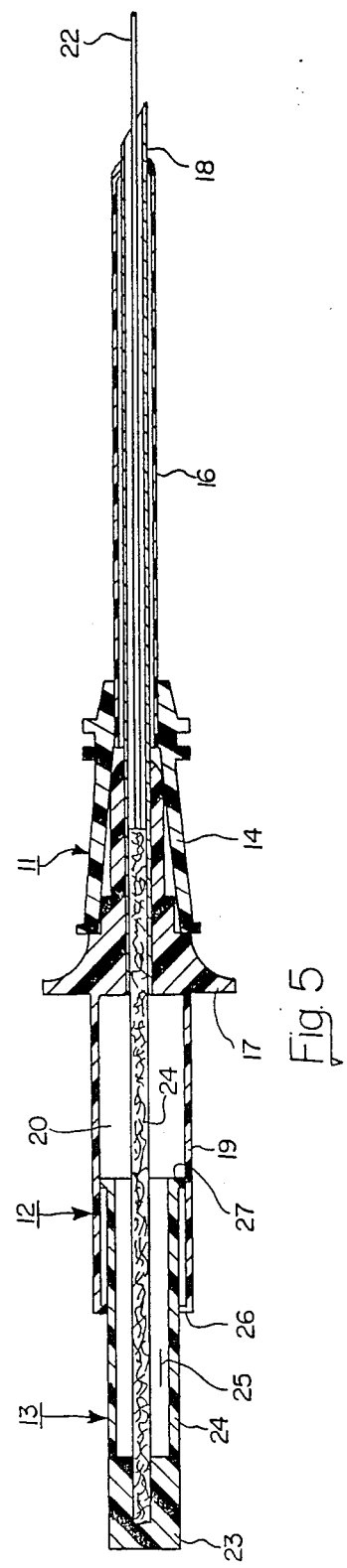

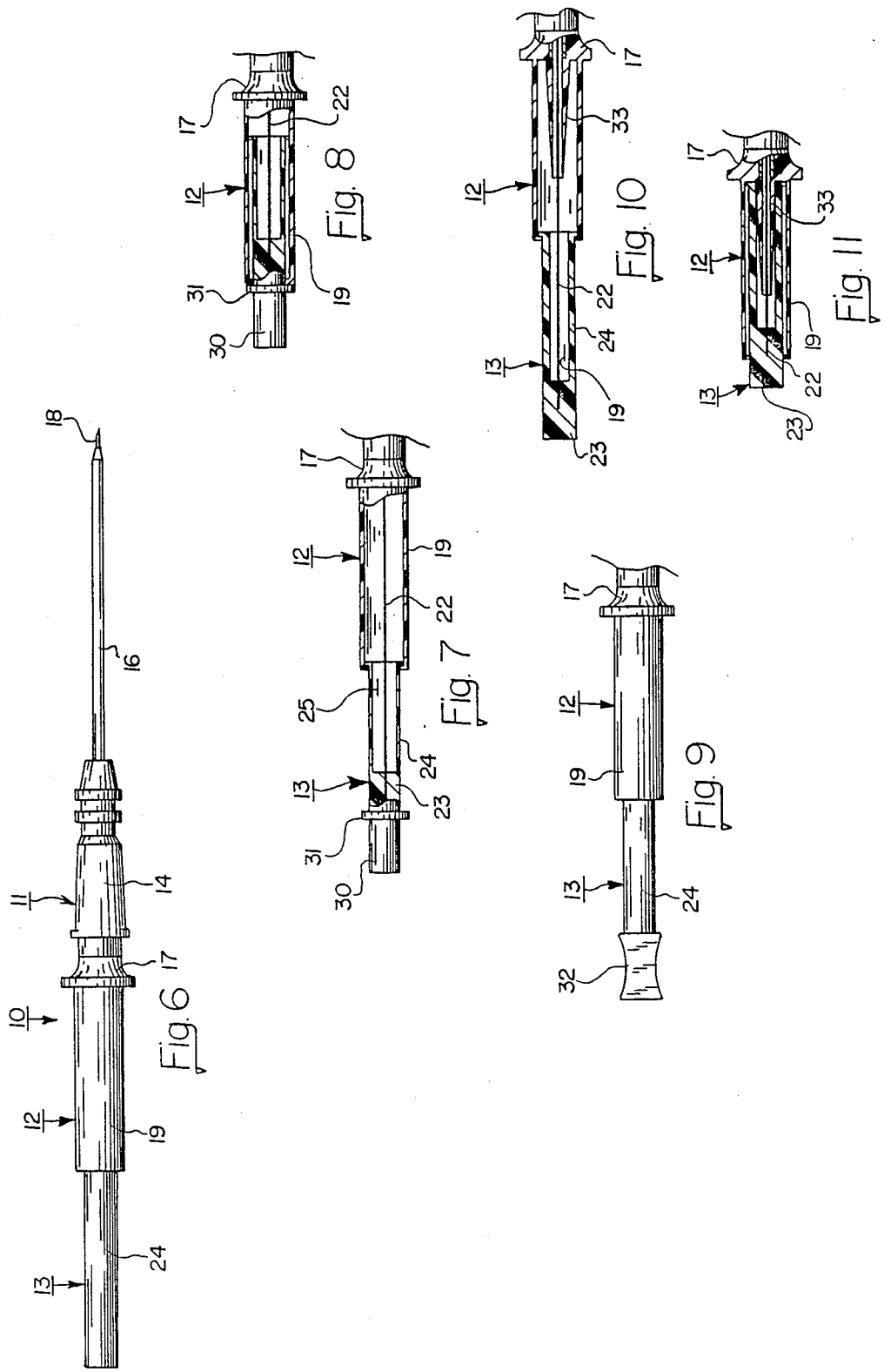

CATHETER ASSEMBLY

This assembly relates to a catheter assembly. More particularly, this invention relates to an over-the-needle catheter assembly.

Heretofore, various types of catheter assemblies have been known for implanting of a catheter in a blood vessel of a body. In cases where the catheter is to be implanted in an artery, the catheter assemblies have usually been constructed as an over-the-needle catheter with a guide wire in order to ensure proper implantation of a catheter. In addition, a flashback chamber has usually been provided to indicate to the user when an artery has been pierced by the appearance of blood within the flashback chamber.

For example, U.S. Pat. No. 4,417,886 describes an over-the-needle type catheter which employs a hollow needle, a guide wire for passage through the hollow needle and a catheter which is slidably mounted on the needle. When in use, the needle is first penetrated into an artery and, with the appearance of blood in the flashback chamber, the guide wire is then moved forwardly into and through the hollow needle and, thence, into the artery a short distance. Thereafter, the catheter can be slid along the needle while guided by the needle and exposed guide wire and implanted in the artery. Thereafter, the needle and guide wire are removed from within the catheter leaving the catheter in place.

As further described, the construction is provided with an actuating handle for the guide wire which projects through a longitudinally extending slot in the guide wire mounting. Because of the slot, any excessive flow of blood into the flashback chamber may pass through the slot to the surrounding environment. Further, the guide wire must be moved over a relatively long path relative to the hollow needle in order to be extended distally past the needle when in use. As a result, the overall structure is relatively long and cumbersome to use.

Other over-the-needle catheters have also been known from U.S. Pat. Nos. 4,525,157; 4,652,256 and 4,655,750. In these constructions provision is made to prevent the escape of blood from a flashback chamber, by mounting a guide wire in a collapsible bag or envelope. However, each describes a structure which utilizes a relatively long wire guide which renders the structures somewhat cumbersome to use.

Accordingly, it is an object of the invention to provide a catheter assembly which employs a relatively short guide wire and which is of relatively compact construction.

It is another object of the invention to provide a catheter assembly which is constructed as a closed system so as to preclude an escape of blood from within a flashback chamber.

It is another object of the invention to provide a guide wire unit and needle unit which can be retrofitted into existing catheters.

It is another object of the invention to provide a closed system catheter wherein proper operation may be verified prior to use.

It is another object to provide a closed system catheter wherein incorrect positioning of a guide wire after a verification procedure is easily detected.

Briefly, the invention provides a catheter assembly comprised of a catheter unit, a needle unit and a guide wire unit.

The catheter unit is constructed to include a catheter and is of any suitable known construction.

The needle unit is removably mounted in the catheter unit and includes a hollow needle extending coaxially of and within the catheter to a point distally beyond the catheter. In addition, the needle unit has a means defining a flashback chamber in communication with the hollow needle.

The guide wire unit is slidably mounted in the needle for movement between a retracted position and an extended position and includes a guide wire having a distal end concentrically within the hollow needle in the retracted position for example, being recessed within the distal end of the needle by a distance of three to six millimeters. Thus, by positioning the guide wire within the hollow needle, a relatively short guide wire unit can be used.

Since the guide wire is initially positioned with the distal end just short of the distal end of the hollow needle, the user need only move the guide wire unit a short stroke distance from the retracted position so as to determine if the guide wire is ready for use. Further, once the hollow needle has pierced a blood vessel, only a short stroke of the guide wire unit is required in order to place an appropriate length of the guide wire in a vessel. For example, a stroke of about one-half inch may be made in order to position the guide wire.

The needle unit may be constructed so that the means defining the flashback chamber is in the form of a sleeve while the guide wire unit is constructed with a hub having a proximal end of the guide wire secured therein and a sleeve extending distally from the hub and slidably within the needle unit sleeve in order to maintain the flashback chamber in sealed relation. Thus, any blood in the flashback chamber may be retained in a sealed condition from the outside environment.

A vent may also be provided in the sleeve of the needle unit or guide wire unit for venting air from the flashback chamber during insertion of the guide wire.

The guide wire is sized relative to the lumen of the hollow needle so as to provide a passage therebetween for a flow of blood. In this respect, the guide wire may have a diameter of up to 80% of the needle lumen diameter. This leaves a sufficient flow passage for blood to flow into the flashback chamber in order to signal that the needle has punctured a vessel.

In order to block: a flow of blood into the flashback chamber once the guide wire has been extended distally beyond the hollow needle, the guide wire may be provided with a thickened portion towards the rear for sealing in a proximal end of the needle. Such a thickened portion may be formed by coating the wire along a proximal section or by providing an enlarged portion at an intermediate point of the wire guide to form the seal.

The needle unit may also include a sleeve which extends proximally of the needle unit hub to serve as a guide for the guide wire.

These and other objects and advantages of the invention will become more apparent from the following detailed description taking in conjunction with the accompanying drawings wherein:

FIG. 1 illustrates a cross sectional view of a catheter assembly constructed in accordance with the invention and in a retracted position;

FIG. 2 illustrates a cross sectional view of the catheter assembly during extension of a wire guide;

FIG. 3 illustrates a cross sectional view of the catheter assembly with a guide wire unit in a fully extended position;

FIG. 4 illustrates a cross sectional view of a modified catheter assembly in a retracted position;

FIG. 5 illustrates a cross sectional view of the catheter assembly of FIG. 4 in a partially extended position;

FIG. 6 illustrates a side view of a catheter assembly constructed in accordance with the invention;

FIG. 7 illustrates a modified catheter assembly employing a vent in the guide wire unit in accordance with the invention;

FIG. 8 illustrates a partial cross sectional view of the catheter assembly of FIG. 7;

FIG. 9 illustrates a partial view of a further modified catheter assembly in accordance with the invention;

FIG. 10 illustrates a further modified catheter assembly employing a guide sleeve for a wire guide in accordance with the invention; and FIG. 11 illustrates a part cross sectional view of the catheter of FIG. 10 in a fully extended position.

Referring to FIGS. 1 and 6, the catheter assembly includes a catheter unit 11, a needle unit 12 and a guide wire unit 13.

Referring to FIG. 1, the catheter unit 11 has a cylindrical hub 14, for example made of plastic, with a conical inner bore 15 as well as a catheter 16 extending from the distal end of the hub 14. The construction of the catheter unit 11 may be of any known type and need not be further described.

The needle unit 12 is removably mounted in the catheter unit 11 and includes a hub or needle holder 17 which is externally sized so as to fit within the bore 15 of the catheter unit hub 14 in a slide-fit manner as is known. In addition, the needle unit 12 includes a hollow needle 18 extending coaxially of and within the catheter 16 to a sharp point distally beyond the catheter 16. Still further, the needle unit 12 has a means in the form of a sleeve 19 extending proximally from the hub 17 for defining a flashback chamber 20 in communication with the lumen 21 of the needle 18.

The needle holder 17 and sleeve 19 may be formed of one-piece and may be made of a suitable plastic material or any other suitable material. Further, the hollow needle 18 can be mounted in any suitable fixed manner within the holder 17.

The guide wire unit 13 is slidably mounted in the needle unit 12 for movement between a retracted position as shown in FIG. 1 and an extended position as shown in FIG. 3 while moving through intermediate positions as indicated in FIG. 2. The guide wire unit 13 includes a guide wire 22, a hub 23 having a proximal end of the guide wire 22 secured therein, for example by means of an adhesive and a sleeve 24 which extends distally from the hub 23. The wire 22 has a distal end concentrically within a distal portion of the hollow needle 18 in the retracted position indicated in FIG. 1. In this respect, the distal end of the wire 22 terminates a short distance from the terminal distal end of the hollow needle 18, for example, a distance of from 3 to 6 millimeters. In addition, the sleeve 12 of the needle holder 17 is sized so as to permit a stroke of the guide wire unit 13 of about one-half inch so that the guide wire 22 can be extended about that distance from the needle 18 as indicated in FIG. 3.

The sleeve 24 of the guide wire unit 13 is slidably mounted in the sleeve 19 of the needle unit 12 in order to maintain the flashback chamber 20 in sealed relation proximally thereof. In addition, a vent 25 in the form of a slit is provided in the sleeve 13 towards the proximal end for the venting of air during movement of the guide wire unit into the extended position of FIG. 3. Further, a hydrophobic filter (not shown) may be used instead of a vent in order to ensure sealing of the blood within the flashback chamber 20. Alternatively, the hub 23 of the guide wire unit 13 may be a porous plug with a pore size sufficient to act as a hydrophobic filter to permit air to escape during insertion of the wire 22. Also, the hub may be provided with through passages to the outside while a hydrophobic membrane filter is positioned across the passages to permit escape of air.

As indicated in FIG. 1, the needle unit sleeve 12 has an inwardly directed annular flange 26 while the sleeve 24 of the guide wire unit 13 has an outwardly extending flange 27. These flanges 26, 27 are positioned to prevent removal of the guide wire unit 13 from the needle unit 12 while also providing for a sealing relationship between the two sleeves as indicated in FIG. 2.

The hub 23 and sleeve 24 of the guide wire unit 13 may be made of any suitable material such as a plastic material. The guide wire 22 is made of any suitable flexible self-supporting material, such as a steel wire.

In order to use the catheter assembly 10, a trained practitioner may initially move the guide wire unit 13 distally a short distance to ensure that the guide wire 22 is in place. That is, by moving the guide wire unit 13, a short distance of a few millimeters, the distal end of the guide wire can be exposed to view. The guide wire unit 13 would then be retracted and the hollow needle 18 then inserted into a vessel such as an artery. Presuming that the procedure is performed correctly and the needle 18 has penetrated into the lumen of the vessel, the guide wire unit 13 is moved into the extended position so as to move the distal end of the guide wire 22 into and along the lumen of the vessel. Thereafter, the catheter unit 11 would be slid along the hollow needle 18 to push the catheter 16 into the vessel while being guided into place by the guide wire 22 in a known manner. Thereafter, the needle unit 12 and guide wire unit 13 can be removed from the catheter unit 11 with the usual procedures being performed to block a flow of blood out of the catheter unit 11. Thereafter, an administration set or other suitable device can be inserted into the bore 15 of the hub 14 of the catheter unit 11 in the usual manner.

It is to be noted that the positioning of the guide wire 22 within the hollow needle 18 in the retracted position, for example as indicated in FIG. 1, does not block a flow of blood into the flashback chamber 20. In this respect, the flow of blood is initially required in order to signal to the practitioner that a vessel has been penetrated. By maintaining the size of the guide wire 22 less than the size of the lumen 21 of the needle 18, a suitable flow passage for the blood is retained. For example, it has been found that the diameter of the guide wire 22 may be up to 80% of the diameter of the lumen 21 of the needle 18 without blocking a flow of blood into the flashback chamber 20.

It is further noted that the catheter unit 11 is a closed assembly. That if, the assembly is sealed against a flow of blood out of the flashback chamber 20 into the surrounding environment. This is particularly important if the blood of the patient may be contaminated with a contagious virus or the like.

The needle unit 12 and guide wire unit 13 may be provided as a sub-assembly which can be used with existing The overall costs of manufacture of a catheter units. Thus, the overall costs of manufacture of a catheter assembly can be reduced.

Referring to FIGS. 4 and 5, wherein like reference characters indicate likeparts as above, the guide wire unit 13' may employ a guide wire 28 having a thickened portion 29 at the proximal end which is secured in the hub 23 and which is sized to slide into the lumen 11 of the needle 18 to seal the lumen against the flow of blood. As indicated in FIG. 5, the diameter of the thickened portion 29 may be of substantially the same size as the diameter of the lumen 21 of the needle 18 so as to extend a distance into the needle 18 for sealing purposes Alternatively the thickened portion 29 may be of a length to simply abut against the proximal end of the needle 18 when the guide wire unit 13, is in a fully extended position (not shown).

Referring to FIGS. 7 and 8, wherein like reference characters indicate likeparts as above, the vent 25 may be provided in the sleeve 24 of the wire guide unit 13, for example near the distal end, in order to vent the flashback chamber 20.

As also indicated in FIGS. 7 and 8, the wire guide unit 13 may be provided with a finger grip 30 at the proximal end with an annular collar 31 for abutting against the needle unit 12 in the fully extended position.

Referring to FIG. 9, wherein like reference characters indicate like parts as above, the wire guide unit 13 may be provided with a finger grip 32 having contoured surfaces for accommodating the fingers of a practitioner.

Referring to FIGS. 10 and 11, wherein like reference characters indicate like parts as above, the needle unit 12 may include an internal sleeve 33 of conical outer shape with a cylindrical bore for slidably receiving the guide wire 22 therein. As indicated, the sleeve 33 may be integral with and extend proximally of the hub 17. When in the extended position, the wire 22 is guided over a relatively long length within the sleeve 33.

By way of example, the guide wire 22 which is used may have a diameter of from 0.006 inches to 0.020 inches while the hollow needle 18 has a lumen 21 of a diameter of from 0.023 inches to 0.025 inches. further, the guide wire 22 may be of a length of from 3 inches to 6 inches while the sleeve 24 of the guide wire unit 13 has a length of ⅜ inches.

The invention thus provides a catheter assembly which is of relatively compact construction and, in particular, of relatively short length.

In addition, the invention provides a catheter assembly which can be readily manipulated by a practitioner for insertion of a wire guide into a vessel in a relatively simple manner.

The invention further provides a closed system catheter assembly for containing any blood which is expelled from an artery during puncture. As such, the risk of infection can be substantially reduced if not eliminated.

What is claimed is:

1. A catheter assembly comprising
   a catheter unit including a catheter;
   a needle unit removably mounted in said catheter unit and including a hollow needle extending coaxially of and within said catheter to a point distally beyond said catheter; and
   a guide wire unit slidably mounted in said needle unit for movement between a retracted position and an extended position, said guide wire unit including a guide wire having a distal end concentrically within a distal portion of said hollow needle in said retracted position and out of said needle in said extended position wherein said needle has a lumen of predetermined diameter and said guide wire is of a smaller diameter to provide a passage therebetween to enable blood to flow to a flashback chamber.

2. A catheter assembly as set forth in claim 1 wherein said guide wire has a diameter of up to eighty percent of said lumen diameter.

3. A catheter assembly as set forth in claim 1 wherein said guide wire has a thickened portion for sealing in a proximal end of said needle in said extended position.

4. A catheter assembly as set forth in claim 1 wherein said needle unit includes a sleeve defining a flashback chamber in communication with said needle and said wire guide unit includes a hub having a proximal end of said guide wire secured therein and a sleeve extending distally from said hub and slidably within said needle unit sleeve to maintain said flashback chamber in sealed relation proximally thereof.

5. A catheter assembly comprising
   a catheter unit including a hollow catheter hub and a catheter extending from said hub;
   a needle unit including a hollow needle hub removably mounted in said catheter hub, a hollow needle extending from said needle hub coaxially of and within said catheter to a point distally beyond said catheter and means defining a flashback chamber in communication with said needle; and
   a guide wire unit including a wire holder slidably mounted in said needle hub for movement between a retracted position and an extended position and a guide wire secured at a proximal end to said wire holder and having a distal end concentrically within a distal portion of said hollow needle in said retracted position and out of said hollow needle in said extended position, sad guide wire having a smaller diameter than a lumen of said needle to provide a passage therebetween to enable of blood to flow to said flashback chamber.

6. A catheter assembly as set forth in claim 5 wherein said guide wire has a diameter of up to eighty percent of said lumen diameter.

7. A catheter assembly as set forth in claim 5 wherein said guide wire has a thickened portion for sealing in a proximal end of said needle in said extended position of said wire holder.

8. A catheter assembly as set forth in claim 5 wherein said means of said needle unit is an open-ended sleeve extending proximally from said needle hub and said wire holder is slidably mounted therein in seal-tight relation.

9. A catheter assembly as set forth in claim 8 wherein said wire holder includes a hub receiving a proximal end of said guide wire therein and a sleeve extending distally of said wire holder hub and slidably within said needle sleeve.

10. A catheter assembly as set forth in claim 9 wherein said sleeves are radially spaced from each other to define a gap therebetween.

11. A catheter assembly as set forth in claim 9 which further comprises a vent in one of said sleeves for venting air therefrom.

12. A catheter assembly as set forth in claim 5 wherein said wire holder includes a collar for abutting said needle unit in said extended position.

13. A catheter assembly as set forth in claim 5 wherein said wire holder includes a finger-grip portion at a proximal end.

14. A catheter assembly as set forth in claim 5 wherein said needle unit includes a sleeve extending proximally of said needle hub and guiding said guide wire therein.

15. A catheter assembly comprising
a catheter unit including a catheter;
a needle unit removably mounted in said catheter unit and including a hollow needle extending coaxially of and within said catheter to a point distally beyond said catheter; and
a guide wire unit slidably mounted in said needle unit for movement between a retracted position and an extended position, said guide wire unit including a guide wire having a distal end concentrically within said hollow needle in said retracted position and out of said needle in said extended position, said guide wire having a thickened portion for sealing in a proximal end of said needle in said extended position.

16. A catheter assembly comprising
a catheter unit including a catheter;
a needle unit removably mounted in said catheter unit and including a hollow needle extending coaxially of and within said catheter to a point distally beyond said catheter and a sleeve defining a flashback chamber in communication with said needle; and
a guide wire unit slidably mounted in said needle unit for movement between a retracted position and an extended position, said guide wire unit including a guide wire having a distal end concentrically within said hollow needle in said retracted position and out of said needle in said extended position, a hub having a proximal end of said guide wire secured therein and a sleeve extending distally from said hub and slidable within said needle unit sleeve to maintain said flashback chamber in sealed relation proximally thereof.

17. A catheter assembly comprising
a catheter unit including a hollow catheter hub and a catheter extending from said hub;
a needle unit including a hollow needle hub removably mounted in said catheter hub, a hollow needle extending from said needle hub coaxially of and within said catheter to a point distally beyond said catheter and an open-ended sleeve extending proximally from said hub to define a flashback chamber in communication with said needle; and
a guide wire unit including a hub, a sleeve extending distally of said wire unit hub and slidably mounted in said needle sleeve in seal-tight relation for movement between a retracted position and an extended position and a guide wire secured at a proximal end to said hub and having a distal end concentrically within said hollow needle in said retracted position and out of said hollow needle in said extended position.

18. A catheter assembly as set forth in claim 17 wherein said sleeves are radially spaced from each other to define a gap therebetween.

19. A catheter assembly as set forth in claim 17 which further comprises a vent in one of said sleeves for venting air therefrom.

20. A catheter assembly comprising
a catheter unit including a catheter;
a needle unit removably mounted in said catheter unit and including a hollow needle extending coaxially of and within said catheter to a point distally beyond said catheter and a proximally extending sleeve for defining a flashback chamber in communication with said needle; and
a guide wire unit slidably mounted in said needle unit for movement between a retracted position and an extended position, said guide wire unit including a hub, a sleeve extending from said hub and slidably mounted in said sleeve of said needle unit and a guide wire secured at a proximal end in said hub and extending into said hollow needle in said retracted position.

21. A catheter assembly as set forth in claim 20 wherein at least one sleeve has a vent for venting air therefrom.

22. A catheter assembly as set forth in claim 20 wherein said sleeve of said needle unit and said sleeve of said guide wire unit are in sealed relation to close said flashback chamber.

* * * * *

UNITED STATES PATENT AND TRADEMARK OFFICE
CERTIFICATE OF CORRECTION

PATENT NO. : 4,863,431

DATED : September 5, 1989

INVENTOR(S) : VINCENT L. VAILLANCOURT

It is certified that error appears in the above-identified patent and that said Letters Patent is hereby corrected as shown below:

```
Column 2, line 48 cancel ":"
Column 4, line 12 cancel ":"
Column 4, line 64 change "if" to -is-
Column 5, line 4 cancel "The ... of a"
Column 5, line 8 "change "likeparts" to -like parts-
Column 5, line 16 after "purposes" insert -.-
Column 5, line 19 change "13" to -13'-
Column 5, line 22 change "likeparts" to -like parts-
Column 5, line 47 change "further" to -Further-
Column 6, line 42 change "sad" to -said-
```

Signed and Sealed this

Twenty-seventh Day of August, 1991

Attest:

HARRY F. MANBECK, JR.

Attesting Officer

Commissioner of Patents and Trademarks